United States Patent [19]
Bastyr et al.

[11] Patent Number: 5,487,759
[45] Date of Patent: Jan. 30, 1996

[54] NERVE STIMULATING DEVICE AND ASSOCIATED SUPPORT DEVICE

[76] Inventors: Charles A. Bastyr, 12476 Rue Fountain Bleau, San Diego, Calif. 92131; Paul T. Kolen, 7212 Linden Ter., Carlsbad, Calif. 92009

[21] Appl. No.: 77,349

[22] Filed: Jun. 14, 1993

[51] Int. Cl.⁶ ......................................................... A61N 1/18
[52] U.S. Cl. ............................ 607/149; 607/115; 607/46; 607/48; 607/74
[58] Field of Search ..................................... 128/639, 644; 607/46, 48, 49, 72, 74, 115, 149, 152

[56] References Cited

U.S. PATENT DOCUMENTS

| | | |
|---|---|---|
| 3,565,080 | 2/1971 | Ide et al. . |
| 4,062,365 | 12/1977 | Kameny . |
| 4,147,171 | 4/1979 | Greene et al. . |
| 4,165,750 | 8/1979 | Aleev et al. . |
| 4,167,189 | 9/1979 | Tachi et al. . |
| 4,210,150 | 7/1980 | James . |
| 4,210,151 | 7/1980 | Keller, Jr. . |
| 4,324,253 | 4/1982 | Greene et al. . |
| 4,338,945 | 7/1982 | Kosugi et al. . |
| 4,340,063 | 7/1982 | Maurer . |
| 4,381,012 | 4/1983 | Russek ..................................... 128/644 |
| 4,387,718 | 6/1983 | Bilitz et al. . |
| 4,408,608 | 10/1983 | Daly et al. . |
| 4,431,002 | 2/1984 | Maurer et al. . |
| 4,509,520 | 4/1985 | Dugot . |
| 4,524,773 | 6/1985 | Fischell et al. . |
| 4,535,777 | 8/1985 | Castel . |
| 4,580,572 | 4/1986 | Granek et al. . |
| 4,583,547 | 4/1986 | Granek et al. . |
| 4,598,713 | 7/1986 | Hansjurgens et al. . |
| 4,632,117 | 12/1986 | James . |
| 4,640,286 | 2/1987 | Thomson . |
| 4,671,286 | 6/1987 | Renault . |
| 4,676,246 | 6/1987 | Korenaga . |
| 4,693,254 | 9/1987 | Mickiewicz et al. . |
| 4,723,552 | 2/1988 | Kenyon et al. . |
| 4,759,368 | 7/1988 | Spanton et al. . |
| 4,793,353 | 12/1988 | Borkan . |
| 4,803,988 | 2/1989 | Thomson . |
| 4,813,418 | 3/1989 | Harris . |
| 4,832,033 | 5/1989 | Maher et al. . |
| 4,890,616 | 1/1990 | Pinckaers . |
| 4,895,153 | 1/1990 | Takeuchi et al. . |
| 4,917,092 | 4/1990 | Todd et al. . |
| 4,919,139 | 4/1990 | Brodard . |
| 4,922,906 | 5/1990 | Takeuchi et al. . |
| 4,922,908 | 5/1990 | Morawetz et al. . |
| 4,926,865 | 5/1990 | Oman . |
| 4,977,895 | 12/1990 | Tannenbaum . |
| 4,989,605 | 2/1991 | Rossen ........................................ 607/46 |
| 5,033,468 | 7/1991 | Takeuchi et al. . |
| 5,036,850 | 8/1991 | Owens . |
| 5,041,974 | 8/1991 | Walker et al. . |

(List continued on next page.)

FOREIGN PATENT DOCUMENTS

| | | | |
|---|---|---|---|
| 3916994 | 11/1990 | Germany .............................. | 607/149 |
| 0008579 | of 1891 | United Kingdom .................. | 607/149 |

OTHER PUBLICATIONS

"Introducing TUWAVE™ the 2 In One Modality", Staodyn, Inc., Longmont, Colo. ©1992.

*Primary Examiner*—George Manuel
*Assistant Examiner*—Jeffrey R. Jastrzab

[57] ABSTRACT

An electrical nerve and an electrical muscle stimulation device used in association with a support unit. The stimulation device is adaptable to be selectively engageable with a plurality of different body braces such that output connectors associated with the stimulation device electrically contact keyed connectors associated with a mounting carrier secured to the particular support unit. The support means includes at least two electrode pads which are selectively positionable at different locations on the support means. The connection between the output connectors of the stimulation device and the keyed connectors applies a stimulation signal to the electrode pads the size of which determines the carrier frequency of the stimulation signal which is impedance matched to the electrode size.

20 Claims, 6 Drawing Sheets

U.S. PATENT DOCUMENTS

| | | |
|---|---|---|
| 5,052,391 | 10/1991 | Silberstone et al. . |
| 5,063,929 | 11/1991 | Bartelt et al. . |
| 5,065,083 | 11/1991 | Owens . |
| 5,069,211 | 12/1991 | Bartelt et al. . |
| 5,117,826 | 6/1992 | Bartelt et al. . |

NERVE STIMULATING DEVICE AND ASSOCIATED SUPPORT DEVICE

BACKGROUND OF THE INVENTION

1. Cross-Reference To Related Application

This patent application is related to U.S. patent application Ser. No. 07/804,455 filed Dec. 10, 1991, by Doctor Paul T. Kolen for a Local Application Micro Processor Based Nerve and Muscle Stimulator which is incorporated herein by this reference.

2. Field Of The Invention

This invention relates generally to Transcutaneous Electrical Nerve Stimulation (TENS) and Electrical Muscle Stimulation (EMS) devices that provides a stimulating waveform that is impedance matched and, more particularly, to a TENS or EMS device in combination with a Support Device such as an orthopedic brace, wrap or support, the combination providing an integrated means of supplying a nerve or muscle stimulation waveform and wherein the TENS or EMS device is keyed to the particular Support Device used and is impedance matched to the electrodes being used.

DISCUSSION OF THE RELATED ART

TENS and EMS devices that apply stimulation signals to a particular area of the human body in order to suppress pain or stimulate a muscle are known in the art. It has been well documented that applying a pulsed waveform, having an adjustable intensity, pulse duration and pulse width, to an afflicted area of tissue to stimulate nerve fibers is effective to suppress pain originating from the immediate area. TENS devices have been used for the symptomatic relief and management of chronic, post-surgical, and post-traumatic acute pain. EMS devices use more powerful waveforms to cause a muscle contraction. These induced muscle contractions are useful in physical therapy for muscle reeducation, retardation of atrophy and increasing a range of motion. For convenience, both TENS and EMS devices will be collectively referred to herein as Stimulation Devices. Where it is necessary to differentiate between the two, the specific device will be mentioned.

In the conventional Stimulation Devices, a pulse generating circuit will generate a pulse waveform having the desirable parameters. A pair of electrodes positioned against a person's skin will apply a bipolar waveform to the skin of the patient. During the positive half of the waveform energy is transferred in one direction to the tissue between the electrodes and during the negative portion of the waveform energy is transferred in the other direction to the tissue between the electrodes. The tissue between the electrodes will act as an electrical load consisting of the skin, muscle and nerve fibers in this area. By varying the frequency, amplitude, pulse width and waveform shape of the stimulation signal a therapist can control the effect that the stimulation signal will have on the nerve between the electrodes. A TENS unit uses a stimulation signal that is strong enough to cause nerve stimulation but which is not strong enough to cause a muscle contraction. EMS, on the other hand, uses a stronger signal and causes the muscle to slowly contract and then release.

Stimulation units are typically plug-in desk top units that are used by doctors and physical therapist at a treatment center or are battery operated and can be used on an out-patent basis. The patient is trained by the doctor or therapist in the procedure of using the TENS unit that is tailored to that individual's need. If the patient wishes to move around during treatment, then the patient must pick up the Stimulation Device and carry the unit or have the device clipped on while the patient is in motion. Otherwise, the patient must remain stationary during the treatment.

SUMMARY OF THE INVENTION

This invention discloses a Stimulation Device (TENS or EMS) used in association with a Support Device. The Stimulation Device is adaptable to be selectively engageable with a plurality of different Support Devices (orthopedic brace or wrap or other garment capable of supporting a Stimulation Device) such that output connectors associated with the Stimulation Device electrically contact keyed connectors associated with a mounting carrier integrated with the particular Support Device. The Support Device includes at least two electrode pads which are selectively positionable at different locations on the Device. The connection between the output connectors of the Stimulation Device and the keyed connectors of the Support Device transfers the stimulation signal to the electrode pads held in position by the Support Device. The keyed connectors of the mounting carrier provide a three-bit binary code that can be used by the Stimulation Device to determine what type of Support Device the Stimulation Device is being connected to and, for instance, the size of the electrodes connected to the Support Device so that the Stimulation Device can adjust the carrier frequency of the stimulation signal so that there is an impedance match between the output waveform of the Stimulation Device and the load (the load corresponding to the impedance of the two electrodes when attached to the patient).

Additional objects, advantages, and features of the present invention will become apparent from the following description and the appended claims, taken in conjunction with the accompanying drawings.

DETAILED DESCRIPTION OF THE PREFERRED EMBODIMENTS

The following description of the preferred embodiment concerning a TENS unit and its associated brace is merely exemplary in nature and is in no way intended to limit the invention, its application or uses. A Support Device is specifically defined as an orthopedic brace or wrap or other garment capable of supporting a Stimulation Device while said Support Device is secured to a person. A Stimulation Device is defined as a portable TENS or EMS device.

Figure 1:
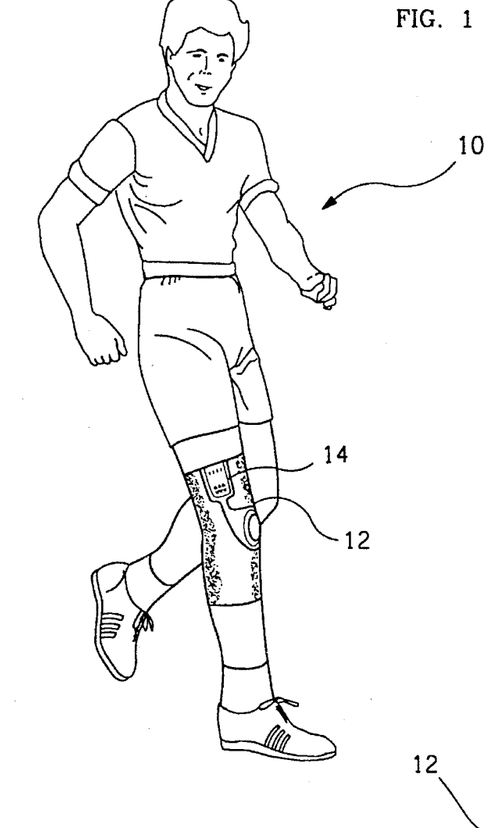
FIG. 1 is a side view of a person wearing a Support Device that is a knee brace incorporating a Stimulation Device according to a preferred embodiment of the present invention.

Turning to FIG. 1, a person 10 is shown wearing a Support Device which in this case is a knee brace 12 generally comprised of a specially shaped neoprene wrap. Neoprene braces of this type are well known in the art. Securely attached to an outer surface of the brace 12, according to a preferred embodiment of the present invention, is a TENS unit 14 for providing stimulation signals to selected portions of the persons skin beneath the brace 12. The stimulation signals are applied to electrodes (see FIG. 3) positioned over an afflicted area in order to suppress pain as a result of any number of different sources of injuries or surgeries. The different sources of pain and injury for which TENS is applicable is well understood in the art and the usefulness of EMS devices during physical therapy for muscle reeducation, retardation of atrophy and for increasing the range of motion are also well understood in the art. Other types of orthopedic braces and wraps for the knee, or other parts of the body, could also be used in association with a Stimulation Devices such as the TENS unit 14 that is shown. Other types of orthopedic braces include, but are not limited to, back braces, shoulder braces, elbow braces as well as sleeves made from various materials such as neoprene and lycra. The TENS unit 14 is shown in this view to illustrate that normal daily activity can be performed while the TENS unit 14 is in use.

Figure 2:
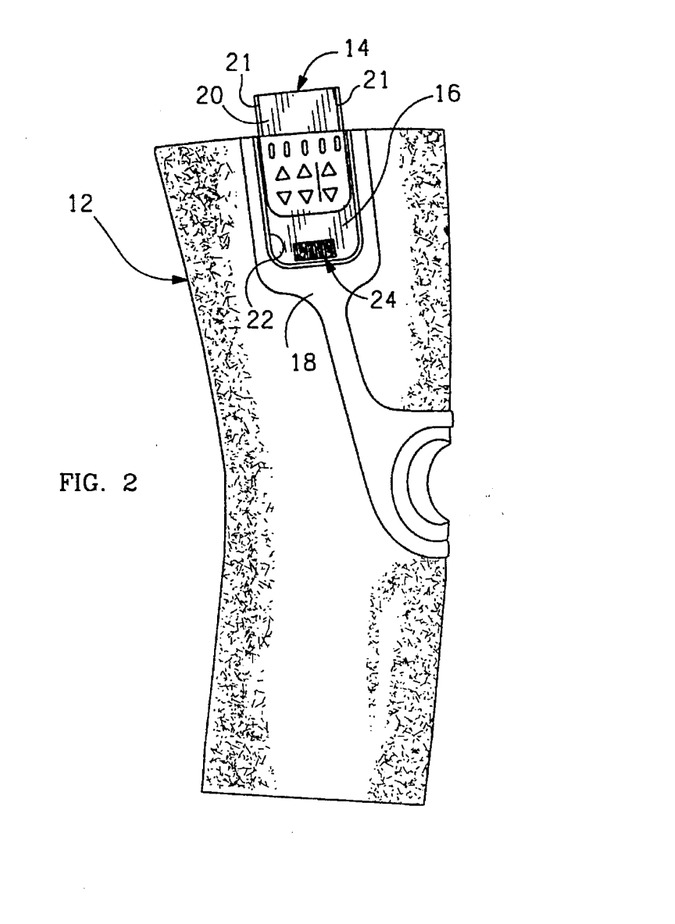
FIG. 2 is an enlarged side view of the knee brace and the associated Stimulation Device of FIG. 1.

FIG. 2 shows an enlarged side view of the knee brace 12 and the associated TENS unit 14. In this figure, the TENS unit 14 is shown partially secured to a support carrier 16. The carrier 16 is a molded plastic structure secured to the neoprene brace 12 in any effective manner. In this example, the carrier 16 is secured to the brace 12 by means of extra neoprene material 18 sewn onto the brace 12 and placed over extended edges (not shown) of the carrier 16 such that the carrier 16 is securely attached to the brace 12. The TENS unit 14 comprises a molded plastic housing 20 for enclosing the different electrical components associated with the unit 14 and shown in schematic form in FIGS. 9, 9A, and 9B. The housing 20 includes molded grooves 21 (not shown) along both sides of the housing 20. The grooves 21 are slidable onto tabs 22 extending towards each other from sidewalls on the carrier 16. In this manner, the TENS unit 14 is readily connected and secured to the brace 12 in a locking engagement. The TENS unit 14 can be secured to the brace 12 in any number of other ways, and can be secured to an inner surface of the brace 12 out of view without departing from the spirit and scope of the invention.

A series of spring-loaded keyed electrical connectors 24 are molded to the carrier 16 at one end, as shown. In a preferred embodiment, there are seven individual pin connectors associated with the keyed connectors 24. First and second pins are for electrical contact to the electrodes for a first channel of the TENS unit 14; the third and fourth pins are for electrical contact to the electrodes of a second channel in the TENS unit 14, and the fifth, sixth and seventh pins are the keyed portion of the connector 24 and are used to generate a binary 3-bit code that can tell the TENS unit 14 what type of Support Device the TENS unit is being inserted into and, for instance, the type or size of electrode that is being used in conjunction with that Support Device. Once the Support Device type and the electrodes size are known by the TENS unit 14 then the TENS unit 14, can adjust its carrier frequency so that there will be an impedance match between the output and the load. This will be discussed in greater detail below. The keyed connectors 24 are electrically connected to the output connectors 92 (see FIG. 4B) associated with the TENS unit 14 when the unit 14 is completely inserted and locked into the carrier 16. The pins of the keyed connectors 24 used for the electrodes are electrically connected to wires (see FIG. 3) which are then electrically connected to the electrodes. As is apparent, the laminate material 18 extends down the brace 12 to support the wires between the brace 12 and the material 18. The operation of the keyed connectors 24 and the associated electrodes will be discussed in greater detail below.

Figure 3:
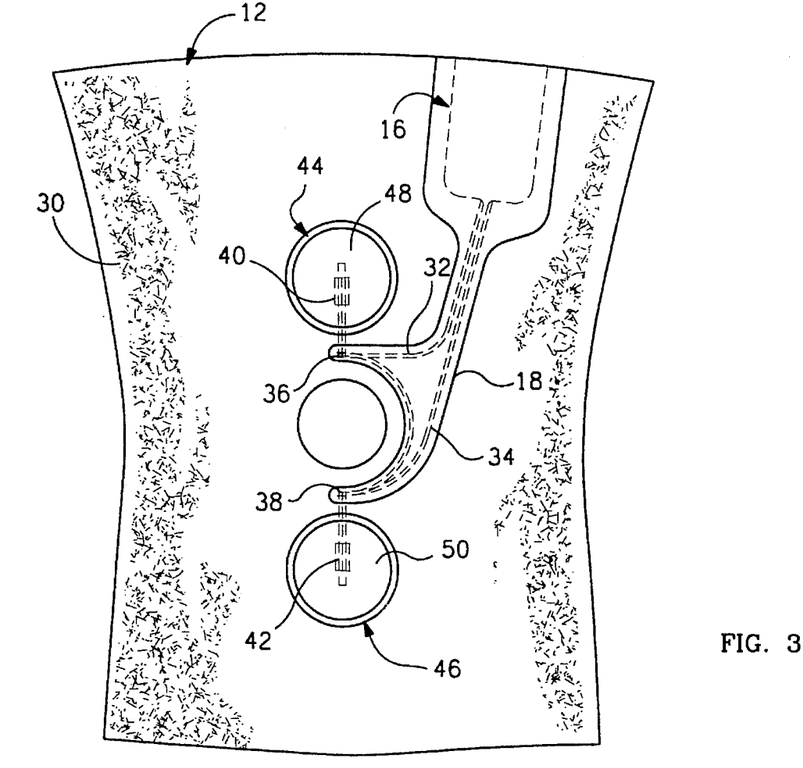
FIG. 3 is an inside front view of the brace of FIG. 1 showing the electrode placement.

FIG. 3 shows an inside view of the brace 12 as if it were cut lengthwise down its back and opened to reveal an inner surface 30 of the brace 12. In this view, the carrier 16 and the material 18 would be on an opposite surface from the surface 30. A first wire 32 and a second wire 34 are shown extending from the carrier 16 along the laminate material 18. The wires 32 and 34 protrude from the surface 30 through holes 36 and 38, respectively. Each of the wires 32 and 34 include an end pin connector 40 and 42, respectively. The pin connectors 40 and 42 are electrically connected to electrode pads 44 and 46, respectively, by sliding the pin connectors 40 and 42 into appropriate connectors associated with the pads 44 and 46. The connectors 40 and 42 connect to the back of the electrode pads 44 and 46 against the surface 30. The electrode pads 44 and 46 represent a first channel for applying one stimulation signal to the skin of the user, but it will be understood that in a preferred embodiment there are two other electrodes pads (not shown) which establish a second channel.

The electrode pads 44 and 46 consist of silicone conductive rubber electrodes covered by a water wicking material 48 and 50, respectively, on a side of the pads 44 and 46 adjacent the user's skin. Additionally, the pads 44 and 46 include a loop material (not shown) on a side towards the surface 30 which can be a pile surface. The water wicking material maintains a layer of water between the skin and the electrode pads 44 and 46 in order to establish a conductive layer in this region. The electrode pads 44 and 46 are removably secured to the surface 30 by means of the loop material. In this manner, the electrode pads 44 and 46 can be placed at virtually any desirable location on the inner surface 30 of the brace 12 within the length of the wires 32 and 34. The electrode pads 44 and 46 can be of any desirable size or shape, with respect to the size and type of the Support Device being used and the desired treatment.

Figure 4A:
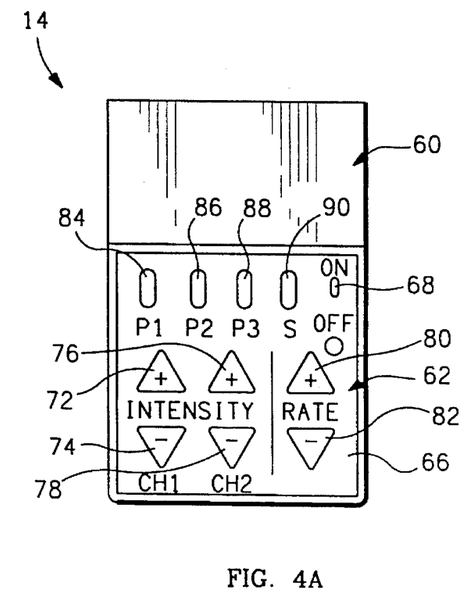
FIGS. 4A and 4B are front and back views of the Stimulation Device unit of FIG. 1.
Figure 4B:
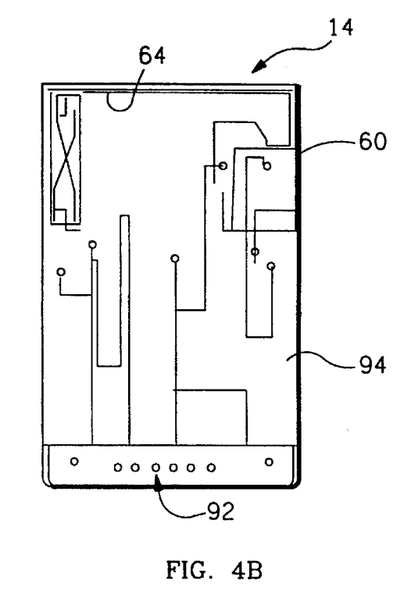

FIGS. 4A and 4B show a front view and a back view of the TENS unit 14, respectively. The TENS unit 14 is separated into a top portion 60 and a bottom portion 62. The top portion 60 typically has a deeper dimension than the bottom portion 62 in order m accommodate a battery pack (not shown) in a battery compartment 64. In one embodiment, the battery pack is two replaceable AA size alkaline batteries or two nickel-cadmium rechargeable batteries that fit into the compartment 64 in order to provide approximately 2.4 to 3.0 volts. The TENS unit 14 could also incorporate throw-away batteries such that the battery compartment 64 could be eliminated. In this alternate embodiment, the TENS unit 14 could be reduced in size to accommodate the battery size. In the embodiment as shown, the TENS unit 14 is approximately 9.68 cm long, 5.88 cm wide and 2.08 cm deep, and weighs about 3.2 oz.

Figure 5:
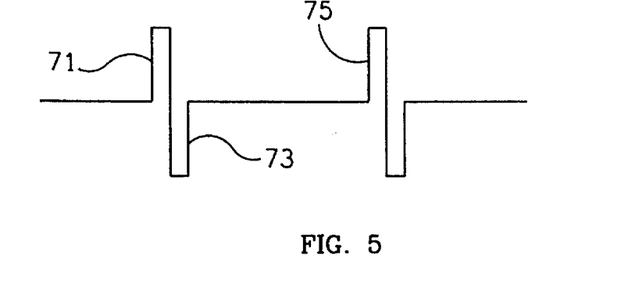
FIGS. 5 through 8 are pulsed output signals from a TENS unit showing different frequency and amplitude variations of the signal.

The bottom portion 62 accommodates the electrical circuitry. A front face 66 of the bottom portion 62 accommodates a number of control keys. Once the TENS unit 14 is inserted into the carrier 16, the unit 14 is operational. A slidable power switch 68 is provided, and when moved to an ON position, an energy output signal will be delivered to the electrode pads 44 and 46. A default output waveform will have a carrier frequency that consists of a high frequency, typically on the order of 2.5 to 3 KHz, that is a bipolar, symmetrical one period signal having a zero net DC component. The carrier frequency is modulated into a low therapeutic frequency, typically on the order of a 2 to 100 Hz pulse train. Such an output signal is shown in FIG. 5. The carrier frequency is the burst of relatively high frequency, one period wave measured between leading edge 71 and trailing edge 73. The therapeutic frequency is the low frequency waveform measured between leading edge 71 of leading edge 75. It is the carrier frequency that establishes the impedance matching between the output signal and the load. The time between the low frequency pulses, represents the time that is allowed for the stimulated nerves to be reset for subsequent firing. The frequency of the 2,500 to 3,000 Hz carrier signal is too fast for the nerve to reset between the individual pulses of the two pulse burst. Therefore, the nerve reacts to the bipolar burst of carrier frequency as if it were in effect one pulse. Because the waveform is alternating current, there is no net direct current component. Therefore, there are no net polar effects to cause long-term positive-negative ion concentrations in the tissue.

The size of the electrodes 44 and 46 determine the effective capacitance that exists when electrodes are coupled to the patient's skin. Put simply, an electrode acts as one plate of a first capacitor and the skin acts as a dielectric. The other electrode acts as the plate of a second capacitor which is effectively connected in series with the first capacitor. When the size of the electrode is increased, it increases the effective surface area of the capacitor plates which, in turn, increases capacitance. As will be discussed below, when this capacitance changes, optimally, the carrier frequency should change so that there is an impedance match between the output of the TENS unit and the patient thereby maximizing the efficient power transfer from the TENS unit to the patient. As will become apparent from the discussion below, for a particular electrode size, the carrier frequency will remain the same. It is the therapeutic frequency and intensity which will be altered by the control keys to give different stimulation results. The waveform parameters of the therapeutic waveform are controlled by the control keys located on the front face 66 of the unit 14, as shown in FIG. 4A. A positive intensity control key 72 and a negative intensity control key 74 increase and decrease the amplitude of the waveform for the first channel. Therefore, in order to increase or decrease the amplitude of the therapeutic waveform, the user need only press the key 72 or the key 74. Likewise, for the second channel, the user need only press an increase intensity key 76 or a decrease intensity key 78. In order to increase the therapeutic frequency, the user presses an increase rate key 80 or a decrease rate key 82. In a preferred embodiment, the frequency varies from 2 pps to 100 pps in sixteen steps. One set of frequency keys 80 and 82 control both channels.

Figure 6:
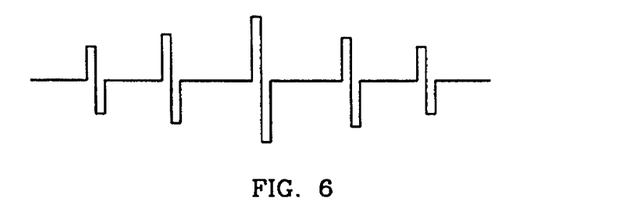

The control keys also include a number of preset program keys. These preset program keys include an intensity surge key 84, a frequency surge key 86, a intensity/frequency surge key 88, and a surge rate key 90. As shown in FIG. 6, by pressing the intensity surge key 84, the therapeutic waveform will have an increasing and decreasing amplitude. As is apparent from this figure, the amplitude of the therapeutic waveform gradually increases to a maximum value, and then gradually decreases to a minimum value. The therapeutic waveform will cycle in this fashion for a particular therapeutic effect.

Figure 7:
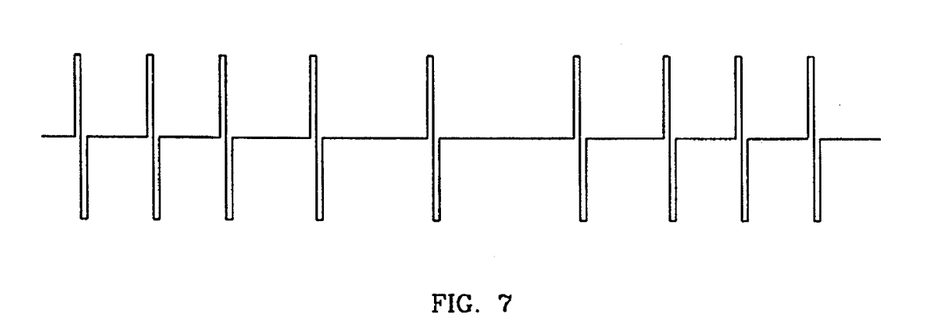

When the frequency surge output key 86 is pressed, the therapeutic waveform will have a decreasing and increasing frequency as shown in FIG. 7. In this figure, the therapeutic waveform continuously cycles from a minimum frequency to a maximum frequency for another therapeutic effect.

Figure 8:
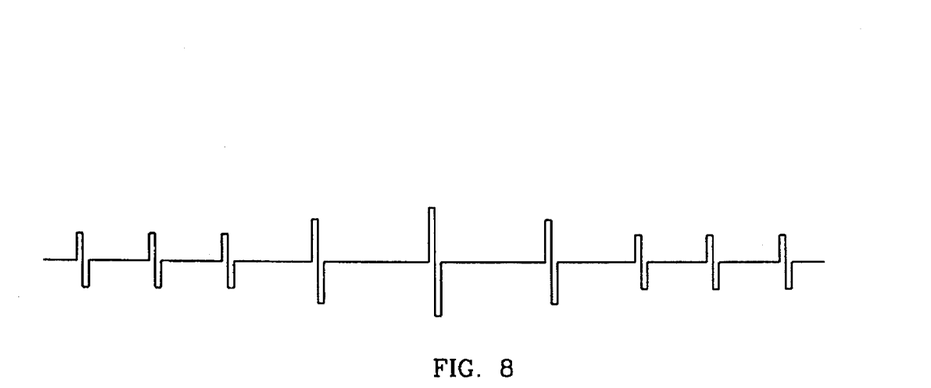

By pressing the intensity/frequency surge rate key 88, the frequency and intensity of the therapeutic frequency vary at the same time. Specifically, as shown in FIG. 8, as the frequency decreases, the amplitude increases, and as the frequency increases, the amplitude decreases for yet another therapeutic effect.

The surge rate key 90 controls how fast each type of varying waveform discussed above cycles. Specifically, the surge rate key 90 controls the surge rate for the intensity surge, the frequency surge, and the intensity/frequency surge. When the user presses the surge rate key 90, each of these rates will jump to either a slow, medium, or fast surge rate. After reaching the fast surge rate, the next time the surge rate key 90 is pressed, the surge rate will jump to the slow rate. When the TENS unit 14 is switched off, the waveform parameters are saved to a non-volatile memory.

As discussed above, the carrier 16 is equipped with seven spring loaded keyed output connectors 24. Four of these connectors are connected to the wire leads and then to the conductive electrode pads. The remaining three connectors are for pad logic. These seven connectors 24 (FIG. 2) align with and connect to seven output pins 92 (FIG. 4B) on a back surface 94 of the TENS unit 14. This binary code on the three pad logic connectors will tell the microprocessor the size of the electrodes so that the microprocessor can cause the frequency generator to generate the appropriate carrier frequency that will impedance match output signal to the electrodes on the skin. In the example above, there are three output connectors which determine the carrier frequency of the output signal. Therefore, there are four different combinations that can represent the electrode size. Of course, more or less connectors could be used in the same fashion which would allow each Support Device to be keyed in a fashion such that when a Stimulation Device is inserted into the carrier 16, the Device will know any desirable characteristics of the Support Device including the type of brace, the electrode size, and, for instance, a particular therapy that is desired. In this manner, a Stimulation Device can be attached to a plurality of different Support Devices having different sized electrodes, and be automatically adjusted for the proper carrier frequency for impedance matching. The three pad logic connectors also preform a safety function. If the TENS unit 14 is removed from the carrier 16 then the TENS unit 14 detects that there is no connection to the three pod logic connectors and TENS unit 14 turns itself off.

Figure 9:
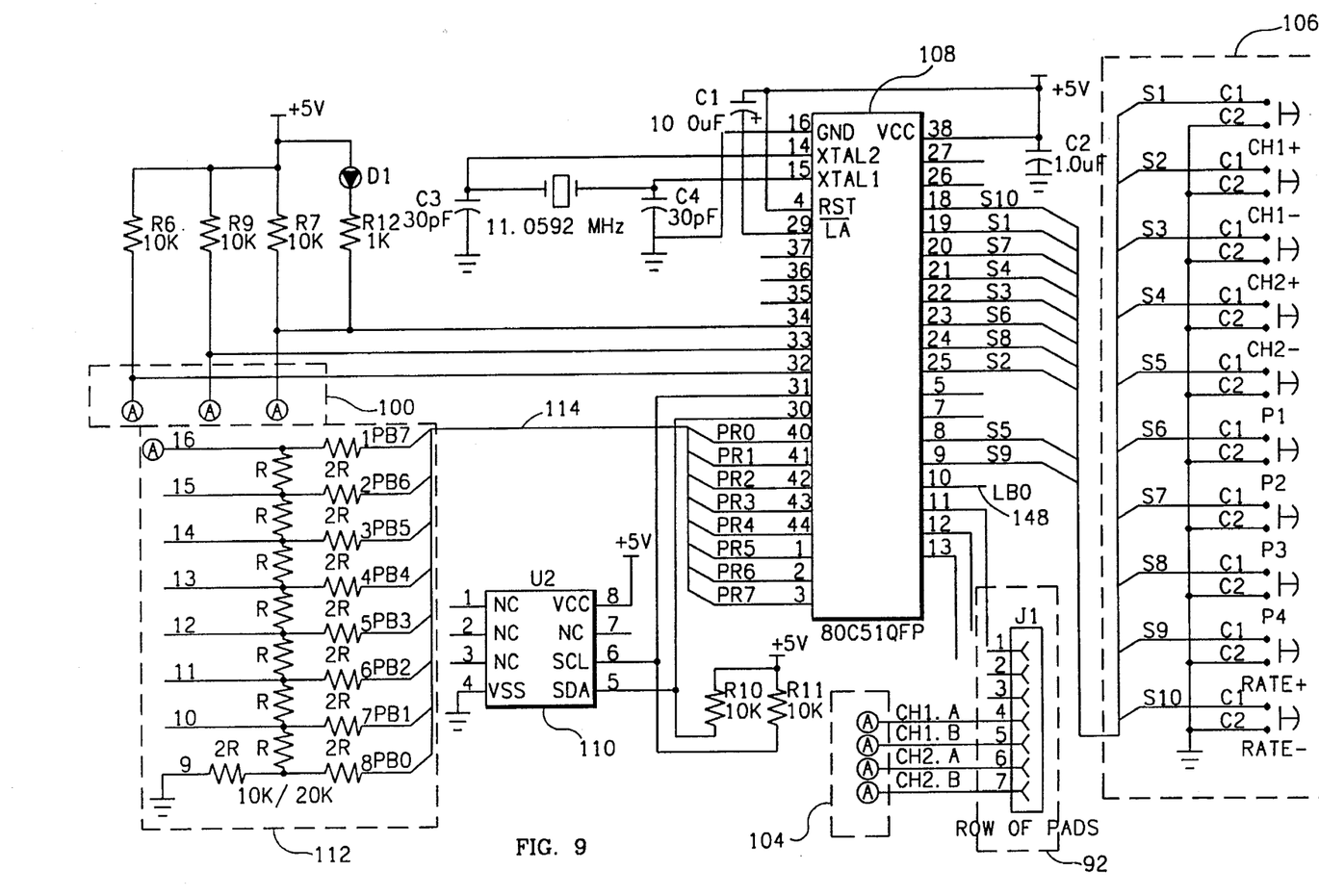
FIGS. 9, 9A, and 9B are schematic diagrams of the circuitry of a TENS unit.
Figure 9A:
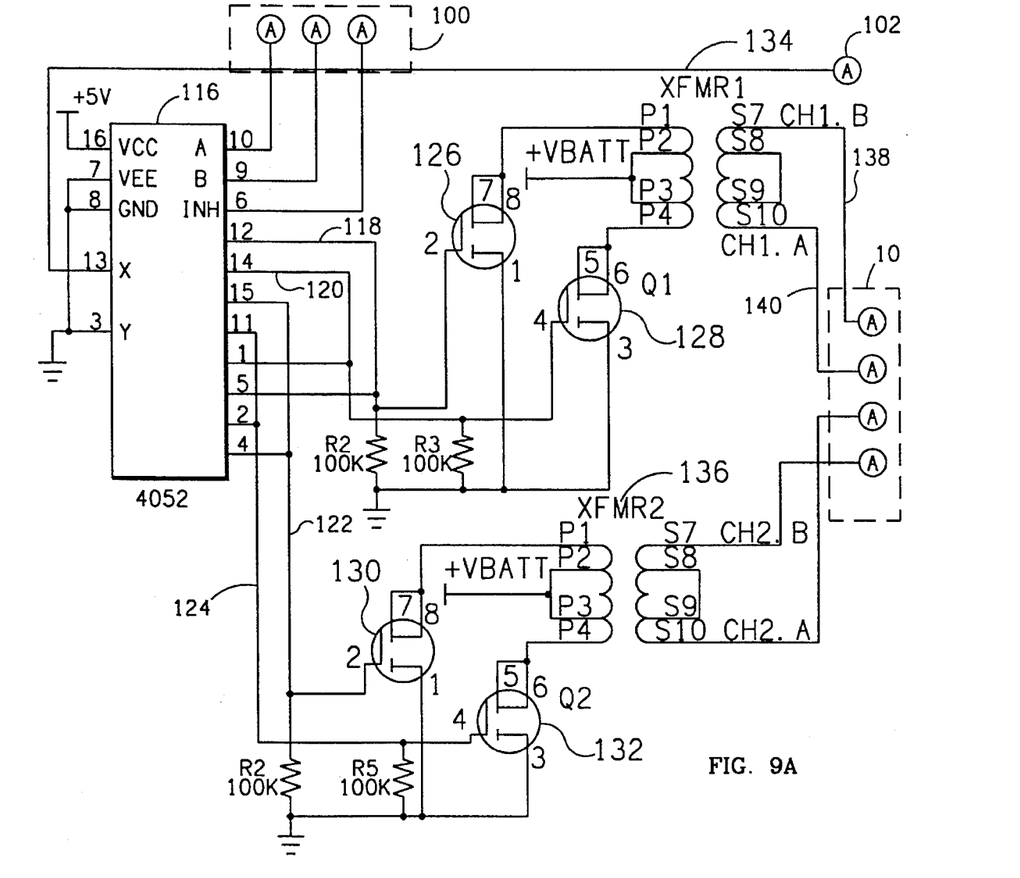
Figure 9B:
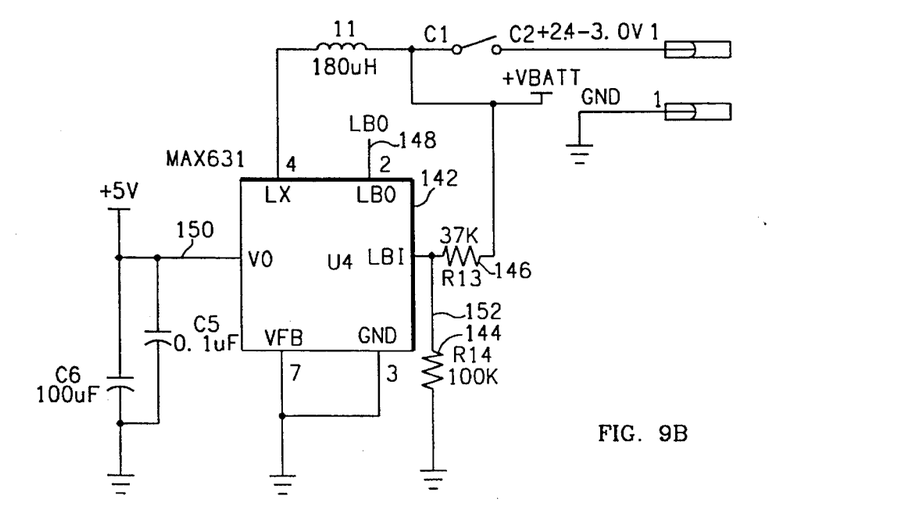

Turning to FIGS. 9, 9A and 9B, a schematic diagram of the TENS circuitry is shown. FIGS. 9, 9A and 9B connect together in the following manner to show a complete circuit diagram for the TENS unit 14. The lines 100 in FIG. 9 connect to the lines 100 in FIG. 9A, the line 102 in FIG. 9 connects to the line 102 in FIG. 9A and the lines 104 in FIG. 9 connect to the lines 104 in FIG. 9A.

In FIG. 9, the control pads in block 106 correspond to the control pads shown in FIG. 4A. The pads 92 in FIG. 9 also correspond to the pads 92 shown in FIG. 4B and represents the connection interface between the TENS unit 14 and the Support Device or, in this case, knee brace 12. The microcontroller 108 is an INTEL 80C51 and is connected as shown in FIG. 9. Memory 110 is $E^2$ PROM and is used as a nonvolatile memory to store the program to set operating parameters and the default parameters. The resistor network 112 acts as a digital to analog converter that receives the digital outputs from lines PB0 through PB7, via buss 114 and converts that digital signal to the analog output on line 102. The range of the analog output on line 102 is 0 through 5 volts. This analog output serves as the intensity control for the output waveforms. The waveform generator 116 in FIG. 9A is a dual four channel analog multiplexor that is made by Motorola. The input on line 102 controls the amplitude of the waveform and control lines 100, which come from the microcontroller 108 in FIG. 9 control the frequency out of the waveform generator 116. In FIG. 9A, the output for channel 1 is on lines 118 and 120 and the output waveform for channel 2 is on lines 122 and 124. Lines 118 and 120 are respectively connected to the output drive transistors 126 and 128. Transistors 126 and 128 are N-channel enhancement mode mosfets made by Siliconix. Typically, the signal on line 118 will go from zero to its preselected intensity level as determined by the signal on line 102, and it will stay high for a period of time and be shut off. Almost at the same time, the signal on line 120 will go high causing the transistor 128 to turn on and pull the signal applied to the primary of transformer 134 in the opposite direction. When the waveform on line 120 goes to zero, transistor 128 turns off and causes the output voltage to fall to zero. Transformer 134 is a 1 to 29 step up, push pull transformer which produces an output waveform across lines 138 and 140 substantially as shown in FIG. 5. Channel 2 operates in an identical I fashion as Channel 1. If the amplitude of the waveform on Channel 1 is different from that on Channel 2, then before Channel 2 is turned on, the microcontroller 108 will send a different digital signal to the digital-to-analog converter 112 causing the analog voltage on line 102 to change to the preselected value prior to the time a signal is put on line 122 thereby initializing the output waveform for Channel 2. The microcontroller 108 in FIG. 9 multiplexes between Channel 1 and Channel 2 to provide waveforms with the same frequencies in Channels 1 and 2. However, the amplitudes of the waveforms in Channels 1 and 2 can be independently varied. The Channel 1 and 2 outputs on lines 104 are connected to the Channel 1 and 2 output lines in FIG. 9 which are connected to output connectors 92 in FIG. 9. Pads 1, 2 and 3 in block 92 on connector J1 are the pad logic keys that can be used to receive a three-bit binary code that can tell the microprocessor which type of electrode is connected to the Support Device and for instance, what type of Support Device is being used. The microcontroller 108 can thereafter make adjustments in carrier frequency and treatment mode for instance, to provide an output carrier frequency which is impedance matched to the load, represented by the two electrodes connected to the patient.

FIG. 9B is a schematic diagram of a step-up voltage regulator 142 which in this instance is a Maxim 631 that steps up the voltage from 2 AA alkaline batteries, in series producing 3 volts, to 5 volts. The output voltage of 5 volts on line 150 is connected to all the various components in the circuit requiring 5 volts. The resistor network formed by resistors 144 and 146 to supply a voltage reference on line 152 which is connected to the low battery lead on the step up regulator 142. When a fallen battery voltage causes the reference voltage on line 152 to go below 1.76 volts then a signal on line 148 tells the microprocessor 108 in FIG. 9 that the battery voltage is too low and that the microcontroller 108 should begin to shut down in an orderly fashion. This prevents the microcontroller 108 from generating random signals when the battery voltage is too low for the microcontroller 108 to function properly.

Figure 10:
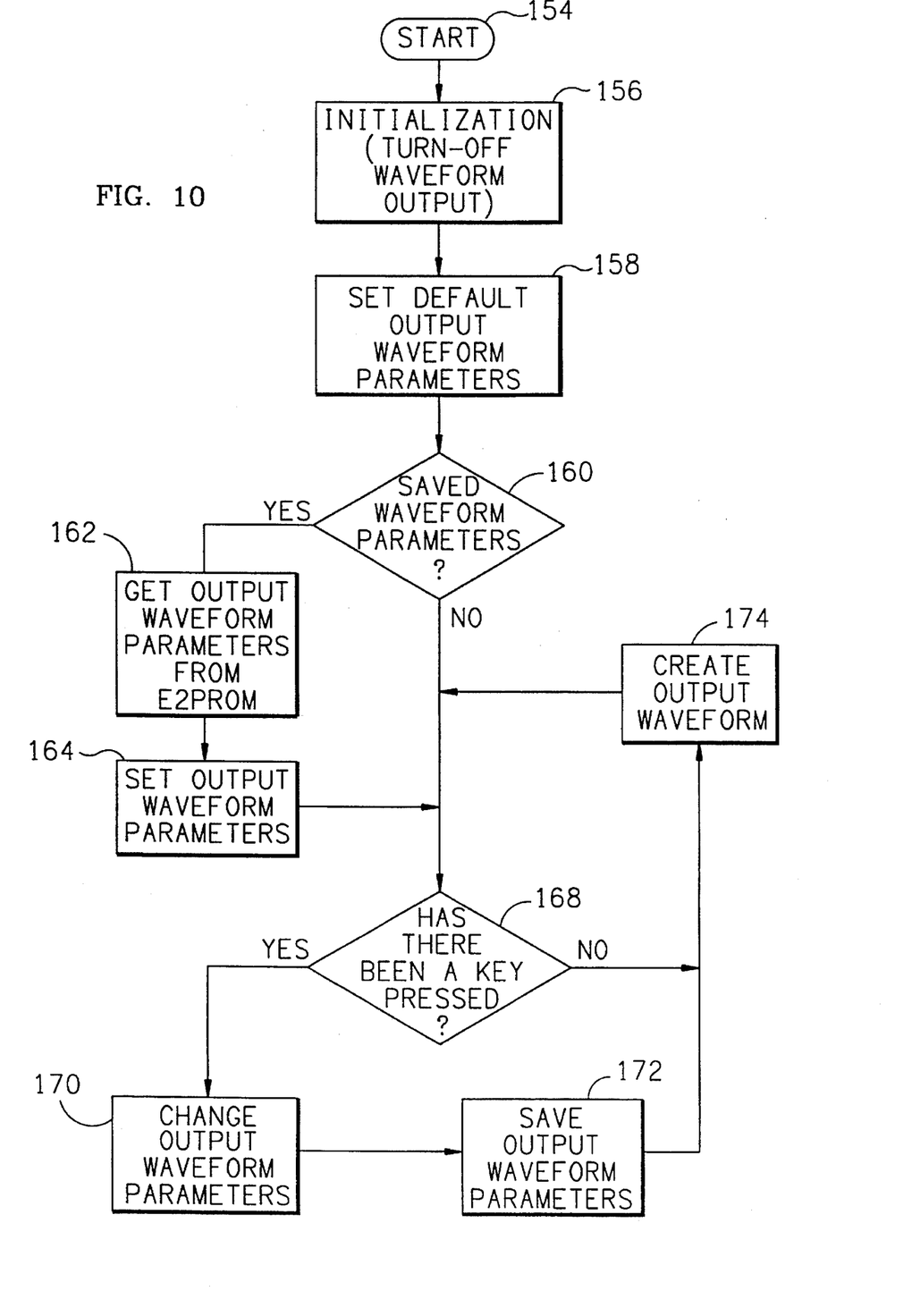
FIG. 10 is a software flow diagram for a TENS unit.

FIG. 10 is a software flow diagram for the overall operation of a TENS Stimulation Device. In block 154 the unit is activated by turning the power switch to the on position. In block 156 the unit turns off the waveform output to the patient. In block 158 the unit sets the default waveforms. The default waveforms are used if the unit has never been turned on or if previously saved waveforms do not fall within a predetermined range. The purpose of the default waveforms is to insure that the user will not receive a strong signal immediately upon activation of the unit.

In block 160 the unit determines if waveforms have been saved. "Saved" waveforms are the waveforms that the patient was using when the unit was last turned off. If the waveforms have been saved then the unit proceeds to block 162 which retrieves the waveforms and to block 164 which sets the output waveform parameters. The unit then proceeds to block 168 which determines if any of the setup keys have been depressed. If not, then the unit proceeds to block 174 and creates and implements the saved waveform.

If it is determined in block 160 that no waveforms have been saved or if "saved" waveforms are not within a predetermined range, then the unit proceeds directly to block 168 with the default waveforms. If no buttons have been pressed then the default waveforms are initialized in block 174. If some of the input pads have been depressed then the unit proceeds to block 170 which changes the output waveform accordingly. The output waveforms is saved in block 172 and then the unit proceeds to block 174 to initialize the new output waveform.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An electrical stimulation system for applying a stimulation signal to a human user, said system comprising:

stimulation means for generating modulated electrical signals having a waveform of predetermined amplitude and therapeutic frequency;

support means removably attachable to a human user for carrying said stimulation means in proximity to said human user, said support means including a connection means for physically and electrically connecting said stimulation means to said support means;

a plurality of electrode pads of a predetermined size disposed on said support means so as to be positioned against the skin of said user when the support means is in position on the user; and said connection means electrically connecting the stimulation means to the electrode pads when the stimulation means is connected to the support means;

said connection means including a plurality of keyed connectors, the keyed connectors being configured to be representative of said size of the electrode pads, said stimulation means including a plurality of output connectors for engaging with said keyed connectors, said stimulation means including means for modifying the electrical signals in response to the configuration of the keyed connectors so as to match the impedance of said electrode pads.

2. The electrical stimulation system according to claim 1 wherein;

the electrode pads are selectively removable from the support means and positionable at alternate locations on the support means.

3. The electrical stimulation system according to claim 2 wherein;

the electrode pads are comprised of silicone conductive rubber electrodes covered by a water wicking material at a surface disposed adjacent the skin of said user and a loop material covering a surface adjacent the support means, wherein the water wicking material holds water so as to provide a layer of conductive water between the skin and the electrode pads.

4. The electrical stimulation system according to claim 1, wherein;

said connection means including a rigid carrier for accepting the stimulation means, said carrier including said keyed connectors, said stimulation means including output connectors for carrying said electrical signals wherein the output connectors of the stimulation means electrically contact the keyed connectors when the stimulation means is secured to the carrier.

5. The electrical stimulation system according to claim 4 wherein;

at least two of the keyed connectors are connected to the electrode pads.

6. The electrical stimulation system according to claim 4 wherein;

the stimulation means including a microcontroller, said microcontroller selecting a carrier frequency to be impedance matched to an electrical load existing at the skin of the user, being stimulated.

7. The electrical stimulation system according to claim 6 wherein;

said connection means includes eight keyed connectors, wherein two of the keyed connectors are connected to electrode pads of a first channel of the system, two of the remaining keyed connectors are electrically connected to electrode pads for a second channel and the remaining three keyed connectors represent a three-bit code for determining the size of said electrode pads.

8. The electrical stimulation system according to claim 1 further comprising:

a plurality of keys coupled to the stimulation means including a first intensity control key and a second intensity control key, wherein the first intensity control key increases the waveform amplitude and the second intensity control key decreases the waveform amplitude.

9. The electrical stimulation system according to claim 1 further comprising:

a plurality of keys coupled to the stimulation means including a first frequency control key and a second frequency control key, wherein the first frequency control key increases the therapeutic frequency of the waveform and the second frequency control key decreases the therapeutic frequency of the waveform.

10. The electrical stimulation system according to claim 1 further comprising:

a plurality if keys coupled to the stimulation means including, an intensity surge key, an intensity/frequency surge key, a strength duration surge key, and a surge rate key, wherein the intensity surge key increases and decreases the amplitude of the therapeutic frequency of the waveform, the frequency surge program key increases and decreases the therapeutic frequency of the waveform, the intensity/frequency surge key alters the amplitude and frequency of the therapeutic waveform such that as the frequency decreases the amplitude increases and as the frequency increases the amplitude decreases.

11. The electrical stimulation system according to claim 1 wherein;

the stimulation means includes a removable power source for providing power.

12. An electrical stimulation system for applying a stimulation signal to living tissue, said system comprising:

stimulation means for applying electrical signals to living tissue, said stimulation means being adapted to be physically and electrically connected to a support means;

support means removably attachable to a human user for carrying said stimulation means in proximity to a human user, said support means including a connection means for physically and electrically connecting said stimulation means to said support means;

said connection means including a rigid carrier for accepting the stimulation means; and wherein the support means comprises a neoprene brace and the carrier is constructed of molded plastic, the carrier being attached to the support means, and wherein the stimulation means includes grooves, and the support means includes tabs which engage with the grooves when the stimulation means is secured to the carrier.

13. An electrical stimulation system comprising:

electrical stimulation device removably inserted into a support device adapted to be connected to a human body, said support device including a plurality of electrode pads;

securing means allowing the stimulation device to be secured to the support device;

a series of keyed connectors on the support device;

a series of output connectors on the electrical stimulation device, said output connectors electrically connected to said series of keyed connectors on the support device when the stimulation device is secured to the support device, wherein a plurality of the output connectors are connectable to said plurality of electrode pads;

pulse generating means for generating a stimulation signal, wherein the stimulation signal is a therapeutic waveform having an amplitude and a therapeutic frequency and a carrier frequency; and a predetermined number of the output connectors being engageable with a predetermined number of the keyed connectors in the support device, the keyed connectors in the support device being configured to be representative of the size of the electrode pads; said pulse generating means including means for generating a stimulation signal having a predetermined carrier frequency that is impedance matched to said electrode pads in response to said keyed connectors' configuration.

14. The system according to claim 13, further comprising;

a plurality of keys coupled to the electrical stimulation device including a first intensity control key and a second intensity control key, wherein the first intensity control key increases the therapeutic waveform amplitude and a second intensity control key decreases the therapeutic waveform amplitude.

15. The system according to claim 13, further comprising;

a plurality of keys coupled to said electrical stimulation device including a first frequency control key and a second frequency control key, wherein the first frequency control key increases the therapeutic frequency of the waveform and the second frequency control key decreases the therapeutic frequency of the waveform.

16. The system according to claim 13, further comprising;

an intensity surge key coupled to said electrical stimulation device, said intensity surge key operable to increase and decrease the amplitude of the therapeutic frequency of the waveform.

17. The system according to claim 13, further comprising;
a frequency surge key coupled to said electrical stimulation device, said frequency surge key operable to increase and decrease the therapeutic frequency of the waveform in a cyclical fashion.

18. The system according to claim 13, further comprising;
a intensity/frequency surge key coupled to said electrical stimulation device, said intensity/frequency surge key operable to alter the amplitude and frequency of the therapeutic frequency of the waveform in a cyclical fashion such that as the therapeutic frequency decreases, the amplitude increases and as the therapeutic frequency increases, the amplitude decreases.

19. The system according to claim 13, further comprising;
said therapeutic waveform having a cycle rate and said stimulation device including:
a surge rate key coupled to said electrical stimulation device, said surge rate key controlling the cycle rate for each type of varying therapeutic waveform.

20. An electrical stimulation system comprising:
electrical stimulation device removably inserted into a support device adapted to be connected to a human body, said support device including a plurality of electrode pads;

a series of output connectors, said output connectors electrically connected to said series of keyed connectors on the support device when the stimulation device is secured to the support device, wherein a plurality of the output connectors are connectable to said plurality of electrode pads;

pulse generating means for generating a stimulation signal, wherein the stimulation signal is a therapeutic waveform including a therapeutic frequency and a carrier frequency, said stimulation device having a housing; and securing means comprising a first groove on a first side of said housing and a second groove on a second side of the housing for securing said housing to said support device, said support device having tab portions engageable with said grooves.

* * * * *